United States Patent
Stamps

(10) Patent No.: US 11,833,336 B2
(45) Date of Patent: Dec. 5, 2023

(54) SYRINGE AND KIT FOR ADMINISTERING PREDETERMINED SPECIFIC EPINEPHRINE DOSES

(71) Applicant: Nancy C. Stamps, Estero, FL (US)

(72) Inventor: Nancy C. Stamps, Estero, FL (US)

(*) Notice: Subject to any disclaimer, the term of this patent is extended or adjusted under 35 U.S.C. 154(b) by 0 days.

(21) Appl. No.: 16/740,074

(22) Filed: Jan. 10, 2020

(65) Prior Publication Data

US 2020/0261659 A1 Aug. 20, 2020

Related U.S. Application Data

(60) Provisional application No. 62/807,563, filed on Feb. 19, 2019.

(51) Int. Cl.
| | | |
|---|---|---|
| *A61M 5/315* | (2006.01) | |
| *A61M 5/00* | (2006.01) | |
| *A61K 31/137* | (2006.01) | |
| *A61M 5/31* | (2006.01) | |

(52) U.S. Cl.
CPC ........ *A61M 5/31591* (2013.01); *A61M 5/002* (2013.01); *A61K 31/137* (2013.01); *A61M 2005/3126* (2013.01)

(58) Field of Classification Search
CPC .............. A61M 5/31591; A61M 5/002; A61M 2005/3126; A61K 31/137
USPC ........................................................ 604/207
See application file for complete search history.

(56) References Cited

U.S. PATENT DOCUMENTS

| | | | | |
|---|---|---|---|---|
| 9,192,723 | B2* | 11/2015 | Creaturo | A61M 5/3129 |
| 2004/0004019 | A1* | 1/2004 | Busch | A61B 17/3401 |
| | | | | 206/571 |
| 2010/0130961 | A1* | 5/2010 | Tucker | A61M 5/3129 |
| | | | | 604/518 |
| 2015/0073354 | A1 | 3/2015 | Creaturo | |
| 2015/0196714 | A1 | 7/2015 | Creaturo | |
| 2017/0304152 | A1 | 10/2017 | Hernandez | |

OTHER PUBLICATIONS

"The Epinephrine Syringe" uploaded by user "Snap Medical Industries" Retrived from the internet at—https://www.youtube.com/watch?v=uLj0S3CU-Wk&feature=emb_title. on Oct. 16, 2018 (Year: 2018).*

(Continued)

*Primary Examiner* — Phillip A Gray
(74) *Attorney, Agent, or Firm* — Jacob M. Ward; Ward Law Office LLC

(57) ABSTRACT

The present invention relates to a syringe and medical kit, which allow for doses of epinephrine of 0.15 mg or 0.15 mL, 0.3 mg or 0.3 mL, and 0.5 mg or 0.5 mL, the most commonly prescribed doses which are utilized today in treating anaphylaxis or other allergic reactions. Currently, existing syringes may include many markings of ten or more dosages. Although these prior art syringes are useful, it is difficult to use them for a patient who must quickly identify a correct dose level among many other marks. The above problem can be addressed by a syringe design which has only a few dosage markings, which correspond to commonly used standard dosages for children and adults. When used with a standard concentration of 1:1000 epinephrine solution, such a device can rapidly provide a known quantity of medicine to a patient who is in urgent need of it.

1 Claim, 1 Drawing Sheet

(56) References Cited

OTHER PUBLICATIONS

Hhttps://dynarex.com/epirite-syringe-2507, Dynarex EpiRite Syringe, Dynarex; (Year: 2018).* https://dynarex.com/media/attachment/file/6/9/6985-EpiRite-Syringe.pdf, EpiRite Syringe pdf (Year: 2019).*

Epi Kit | Epi Kits | Kits | Bound Tree, Oct. 29, 2018, https://web.archive.org/web/20181029211442/https://www.poundtree.com/Kits/Epi-Kits/Epi-Kit/p/680154-KIT.

Dynarex 6985 EpiRite™ Syringe with Luer Slip—QuickMedical, Date unknown (package indicates manufacturing date to be Jan. 28, 2019), https://www.quickmedical.com/dynarex-epirite-syringe-luer-slip-6985.html.

Stamps, Nancy C., Inventor disclosure to Pitch Tank panel, Jan. 2018.

* cited by examiner

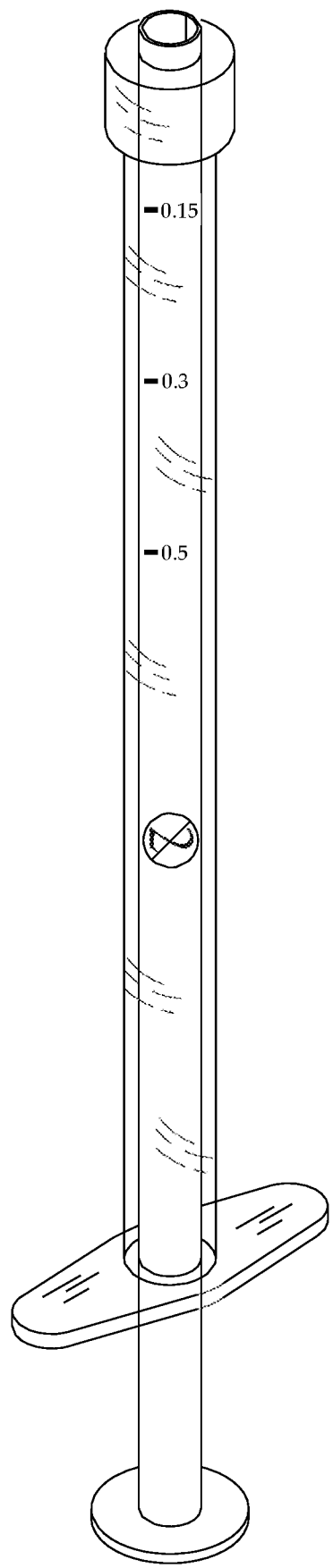

SYRINGE AND KIT FOR ADMINISTERING PREDETERMINED SPECIFIC EPINEPHRINE DOSES

RELATED APPLICATIONS

The present application claims priority from U.S. Provisional Application No. 62/807,563, filed on Feb. 19, 2019.

FIELD OF INVENTION

The present general inventive concept relates to a system for dispensing epinephrine.

BACKGROUND

Epinephrine is a chemical that has proven effective in narrowing blood vessels and opening airways in the lungs. These effects have shown to reverse severe low blood pressure, severe skin itching, wheezing and other symptoms of an allergic reaction. Typically, epinephrine is dispensed with an autoinjector system, the cost of which is high relative to the cost of the chemical. This invention allows medically trained personnel to quickly and accurately fill The Epinephrine Syringe™ and administer a dose of epinephrine for people weighing equal to or greater than 15 kg or 33 lbs.

The EpinephrineSnap® kits described herein meet the needs of trained medical professionals to have epinephrine stocked and ready to go in case of anaphylaxis without having to spend large sums on autoinjectors to deliver the epinephrine. The EpinephrineSnap® kits also provide greater indications for use in that each kit can be utilized to treat anaphylaxis in either an adult or a child weighing equal to or greater than 15 kg or 33 lbs.

Today, standard general practice is to address anaphylaxis or other allergic reactions by using an aqueous solution of epinephrine which has been prepared with a 1:1000 dilution ratio. This results in a solution which has 1 milligram of epinephrine per milliliter of solution. (With this standardized concentration, an epinephrine dose of 0.15 mg corresponds to 0.15 mL of solution, a dose of 0.3 mg corresponds to 0.3 mL, a dose of 0.5 mg corresponds to 0.5 mL, and so on.)

The EpinephrineSnap® kits and The Epinephrine Syringe™ allow for doses of epinephrine of 0.15 mg or 0.15 mL, 0.3 mg or 0.3 mL, and 0.5 mg or 0.5 mL, the most commonly prescribed doses of epinephrine which are utilized today in treating anaphylaxis.

Important advantages result from a syringe design with marks of 0.15 mg or 0.15 mL, 0.3 mg or 0.3 mL, and 0.5 mg or 0.5 mL. These marks correspond to medically recognized doses which are tailored to specific categories of patients, based on their body weight. A user who urgently requires an injection can benefit greatly if a syringe includes these specific dose markings but no other ones. Currently, existing prior art syringes may include many graduated markings of ten or more dosages. Although these prior art syringes are useful for certain applications, it is difficult to use them to rapidly administer (or self-administer) epinephrine to a patient who must quickly identify a correct dose level among many other marks.

The above problem can be addressed by a syringe design which has only a few dosage markings, which correspond to commonly used standard dosages for children and adults. When used with a standard concentration of 1:1000 epinephrine solution, such a device can rapidly provide a known quantity of medicine to a patient who is in urgent need of it.

BRIEF SUMMARY

Example embodiments of the present general inventive concept can provide a syringe device.

When a manufacturer or prescriber determines or predetermines an appropriate epinephrine dose or volumetric dosage for a patient, this can be done based on a "predetermined patient characteristic."

For instance, a predetermined patient characteristic could be body weight of a patient. In such a case, a corresponding dose which is indicated for a body weight of 30 kg/66 lbs. or more might be a dose of 0.3 to 0.5 mg (0.3 to 0.5 mL). A characteristic body weight of 30 kg or 66 lbs. or less could result in a manufacturer or prescriber recommending a volumetric dosage using a 0.01 mg/kg (0.01 mL/kg) ratio, and to calculate corresponding doses from this formula, which is based on a patient's predetermined body weight characteristic.

Example embodiments of the present general inventive concept can provide a single-use device for administering one or more predetermined doses of epinephrine, comprising: a barrel having an internal reservoir configured to contain a volume of epinephrine constituting a single dose according to a manufacturer's or prescriber's recommended dosage of epinephrine; the barrel formed from a translucent material that is configured to transmit light to the reservoir and to provide a visible indication of an amount of epinephrine to be distributed; a plunger configured to be received in the barrel and axially movable relative thereto; the barrel including markings on the barrel indicating volumetric dosage for a predetermined patient characteristic and corresponding dose of the epinephrine calibrated to a manufacturer's or prescriber's recommended dosage; and a needle configured to attach to a distal end of the barrel and in fluid communication with the barrel.

Example embodiments can provide a device wherein said markings on the barrel indicating volumetric dosage comprise specific epinephrine gradients of 0.15, 0.3, and 0.5.

Example embodiments can provide a device wherein the device includes a luer lock.

Example embodiments can provide a device wherein said markings on the barrel indicating volumetric dosage consist of specific epinephrine gradients of 0.15, 0.3, and 0.5.

Example embodiments can provide a device which consists of a 1 mL luer lock syringe with specific epinephrine gradients of 0.15 mL, 0.3 mL, and 0.5 mL.

Example embodiments can provide a medical device kit comprising: multiple Epinephrine Syringes™.

Example embodiments can provide a medical device kit comprising: a syringe for administering a single predetermined dose of epinephrine, the syringe further comprising: a barrel having an internal reservoir configured to contain a volume of epinephrine constituting a single dose according to a manufacturer's or prescriber's recommended dosage of epinephrine, the barrel formed from a translucent material that is configured to transmit light to the reservoir and to provide a visible indication of an amount of epinephrine to be distributed, a plunger configured to be received in the barrel and axially movable relative thereto, the barrel including markings indicating volumetric dosage for a predetermined patient characteristic and corresponding dose of the epinephrine calibrated to a manufacturer's or a prescriber's recommended dosage; a needle configured to attach to a distal end of the barrel and in fluid communication with the barrel; wherein the medical device kit further comprises: a vial containing a predetermined dose of epinephrine; and antiseptic preparation pads for sterilizing an injection site. (Types of antiseptic preparation pads could include alcohol pads. In some embodiments, a kit could also comprise epinephrine, an epinephrine drug package insert, an instructions for use card, and/or packaging for the medical device kit.)

Example embodiments can provide a medical device kit wherein said markings indicating volumetric dosage comprise specific epinephrine gradients of 0.15, 0.3, and 0.5.

Example embodiments can provide a medical device kit, further comprising a luer lock.

Example embodiments can provide a medical device kit wherein said markings indicating volumetric dosage consist of specific epinephrine gradients of 0.15, 0.3, and 0.5.

Example embodiments can provide a medical device kit, further consisting of a 1 mL luer lock syringe with specific epinephrine gradients of 0.15 mL, 0.3 mL, and 0.5 mL Additional features and embodiments of the present general inventive concept will be set forth in part in the description which follows, and, in part, will be obvious from the description, or may be learned by practice of the present general inventive concept.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawing in which:

FIG. 1 illustrates The Epinephrine Syringe™, a syringe for administering a single dose of epinephrine according to example embodiments of the present general inventive concept.

DETAILED DESCRIPTION

Example embodiments of the present general inventive concept provide a new and improved epinephrine convenience kit, utilizing a single use vial of epinephrine of concentration 1 mg/mL for intramuscular or subcutaneous use, an epinephrine package insert, alcohol prep pads, safety needles, The Epinephrine Syringe™ syringes, and an EpinephrineSnap® instructions for use card. Example embodiments may also incorporate varying dosage amounts based on a body weight of a patient.

In some embodiments of the present general inventive concept, The Epinephrine Syringe™, the syringe may consist of a 1 mL luer lock syringe with specific epinephrine gradients of 0.15 mL, 0.3 mL, and 0.5 mL, in order to assist with accurate and standard dosing for patients weighing equal to or greater than 15 kg or 33 lbs.

According to example embodiments of the present general inventive concept, to use the epinephrine convenience kit, the administrator may remove the inner tray from the outer packaging and place the contents on a flat surface. The epinephrine vial may be removed and inspected prior to use for particulate matter and discoloration which may indicate contamination of the epinephrine. The lid of the vial may then be snapped off and a rubber stopper wiped with an alcohol prep pad to prevent contamination. The administrator may then remove the safety needles and one or more syringes, attach a safety needle to a syringe and insert the needle through the rubber stopper of the vial, in order to draw out a single dose. Although injection may be performed at various locations on a patient, in one embodiment, the injection is given in the anterolateral aspect of the patient's thigh. A site of the injection may be cleaned with alcohol prior to use, although the injection may also be given directly through clothing.

Dosage may be repeated per a prescriber's order, or manufacturer's recommendations as necessary, depending upon severity of an allergic reaction and potential effects of the epinephrine. Each EpinephrineSnap® convenience kit is designed to be a single use kit. After treatment has been completed, remaining epinephrine, syringes, and needles may be disposed of.

In some embodiments the syringe will dispense a single dose of epinephrine to the patient for intramuscular or subcutaneous usage. A medication provided in the kit may be a non-selective alpha and beta adrenergic agonist indicated for emergency treatment of allergic reactions including anaphylaxis.

In some embodiments, dosage may be based on age or size of the patient. For example, for adults and children 30 kg or 66 lbs. or more, 0.3 to 0.5 mg (0.3 to 0.5 mL) of epinephrine may be administered intramuscularly or subcutaneously in an anterolateral aspect of the thigh, up to a maximum of 0.5 mg (0.5 mL) per injection, repeated every 5 to 10 minutes as necessary. Health care providers may monitor clinically for reaction severity and cardiac effects. For Children 30 kg or 66 lbs. or less, 0.01 mg/kg (0.01 mL/kg) of epinephrine may be administered intramuscularly or subcutaneously in an anterolateral aspect of the thigh, up to a maximum of 0.3 mg (0.3 mL) every 5 to 10 minutes as necessary. In one embodiment, a maximum single dose may be 0.3 mg (0.3 mL) per injection, repeated every 5 to 10 minutes as necessary. Health care providers may monitor clinically for reaction severity and cardiac effects.

Referring to FIG. 1, a syringe can include a barrel having an internal reservoir configured to contain a volume of epinephrine constituting a single dose according to a manufacturer's recommended dosage concentration of epinephrine. As illustrated in FIG. 1, the barrel can be formed from a translucent material that is configured to enhance transmitted light to the internal reservoir and to provide a clear, visible indication of an amount of epinephrine to be distributed. For example, said translucent material can be configured to enhance transmission of specific color wavelengths, such as green, to provide high visibility of plunger location. Markings on the barrel of the syringe indicating volumetric dosage for a predetermined patient characteristic and corresponding dose of the epinephrine can be calibrated to the manufacturer's or prescriber's recommended dosage, and the markings can interact with the translucent material and plunger color. According to one embodiment of the invention, the markings on the barrel show 0.15 mg or 0.15 mL, 0.3 mg or 0.3 mL, and 0.5 mg or 0.5 mL readings, which indicate a dosage in milligrams and milliliters of the epinephrine (of concentration 1 mg/mL) to be distributed.

Also illustrated in FIG. 1 is a plunger received in the barrel and axially movable relative to the barrel. In some embodiments, the plunger may be constructed of a translucent material as illustrated by the barrel shown in FIG. 1. In other embodiments, the plunger may be constructed of an opaque material. Additionally, the plunger may come in a variety of different colors. The barrel and plunger may be made from polypropylene, polyethylene, or other materials known in the art. The materials can be configured to enhance visibility of the plunger and dosage volume. The barrel can be configured to be attached to a needle for administering a dosage of epinephrine to the patient.

Example embodiments of the present general inventive concept may give a health care provider an ability to administer other injections in addition to epinephrine. Example embodiments of the present general inventive concept possess a compact size, which allows a kit to be stored conveniently and be ready for use. Other features and/or advantages will be recognized in descriptions of example embodiments of the present general inventive concept contained herein. Such a device and system may present enhanced functionality in a host of medical applications such as, for example, hospital visits, EMS operations, mobile medical providers, home health care providers, physician offices, dental practices, etc.

Additionally, some example embodiments of the present general inventive concept comprise a syringe which is adapted to be used a single time. In other example embodiments, a syringe might be adapted to be reused or used more than once before being discarded. Some example embodiments might comprise a kit which, as a whole, is adapted for a single use.

Various example embodiments of the present general inventive concept provide a lightweight and economical device, or accessory, or kit, to allow a medical professional to quickly and accurately fill a syringe and give a shot of epinephrine at a life-saving dose for either an adult or a child with high visibility components, and the kit meets the needs of medical professionals to have epinephrine stocked and ready to go in case of anaphylaxis without having to spend large sums on autoinjectors to deliver said shot of epinephrine.

Such medical procedures can be administered quickly and effectively, eliminating the need to use a costly autoinjector device. Such a device/system increases efficiency while also lowering cost.

What is claimed is:

1. A single-use device for administering one or more predetermined doses of epinephrine, consisting of:
a barrel having an internal reservoir configured to contain a volume of epinephrine constituting a single dose according to a manufacturer's or prescriber's recommended dosage of epinephrine, the barrel formed from a translucent material that is configured to transmit light to the reservoir and to provide a visible indication of an amount of epinephrine to be distributed, wherein said markings on the barrel indicating volumetric dosage consist of numerals and decimal points, arranged to form indicators in the numerical forms of only 0.15, 0.3, and 0.5;
a plunger manufactured from an opaque material having a color configured to enhance visibility of the plunger and dosage volume through the translucent material of the barrel, the plunger configured to be received in the barrel and axially movable relative thereto, the barrel including markings on the barrel indicating volumetric dosage for a predetermined patient characteristic and corresponding dose of epinephrine of concentration 1 mg/mL calibrated to a manufacturer's or prescriber's recommended dosage; and
a leur lock at a distal end of the barrel and configured to receive a needle and place the needle in fluid communication with the barrel.

* * * * *